United States Patent
Bono et al.

(10) Patent No.: US 7,081,117 B2
(45) Date of Patent: *Jul. 25, 2006

(54) LOCKING CAP ASSEMBLY FOR SPINAL FIXATION INSTRUMENTATION

(75) Inventors: Frank Scott Bono, Rehoboth, MA (US); George Joseph Ross, Rehoboth, MA (US); Christopher Werner Sicvol, Braintree, MA (US); Ian Burgess, Barrington, RI (US)

(73) Assignee: DePuy Acromed, Inc., Raynham, MA (US)

( * ) Notice: Subject to any disclaimer, the term of this patent is extended or adjusted under 35 U.S.C. 154(b) by 149 days.

This patent is subject to a terminal disclaimer.

(21) Appl. No.: 10/828,508

(22) Filed: Apr. 20, 2004

(65) Prior Publication Data

US 2005/0033296 A1    Feb. 10, 2005

Related U.S. Application Data

(63) Continuation of application No. 09/667,937, filed on Sep. 22, 2000, now Pat. No. 6,755,829.

(51) Int. Cl.
  *A61B 17/56*  (2006.01)
(52) U.S. Cl. ......................................................... 606/61
(58) Field of Classification Search .................. 606/61, 606/53, 72
  See application file for complete search history.

(56) References Cited

U.S. PATENT DOCUMENTS

| 4,950,269 A | 8/1990 | Gaines |
| 5,257,993 A | 11/1993 | Asher et al. |
| 5,261,912 A | 11/1993 | Frigg |

(Continued)

FOREIGN PATENT DOCUMENTS

DE    94 03 231    4/1994

(Continued)

*Primary Examiner*—Eduardo C. Robert
*Assistant Examiner*—Michael J. Araj
(74) *Attorney, Agent, or Firm*—Nutter, McClennen & Fish, LLP

(57) ABSTRACT

An assembly such as an anchor screw, bone plate, offset hook, post, transverse connector or other spinal anchor for anchoring to bone and clamping a linkage such as a rod, wire cable or the like. The assembly has a top member with an open slot to receive the linkage, and a twist-lock closure cap to close the open end, capturing the linkage in the slot. One closure cap fits over and around the top member, with a set of segmented protrusions that extend through a corresponding set of protruding flange segments spaced about the circumference of the top member. The cap is configured to rotate and lock against the top member like a flange-locking bayonet mount when turned through a limited degree of rotation. Slots may be provided through the face of the closure cap allowing reduction tabs to project through the cap, and the locking cap may be adapted to a range of screw, eye, hook, post, connector and other anchor assemblies to securely clamp the linkage by use of a rotation tool disposed along an access path aligned with the axis of the screw, thus requiring no lateral clearance along the longitudinal direction of the linkage element. Locking is effected by a set screw that passes through the cap and tightens against the linkage to firmly immobilize it in the anchor assembly. Another cap embodiment fits into the center of the head with a partial twist locking motion. Opposed locking surfaces prevent slippage in the radial direction, and a sloping contact floor surface may apply torque to further increase pressure on urge mating detent features in an adjacent wall.

68 Claims, 13 Drawing Sheets

U.S. PATENT DOCUMENTS

| | | |
|---|---|---|
| 5,306,275 A | 4/1994 | Bryan |
| 5,346,493 A | 9/1994 | Stahurski et al. |
| 5,443,467 A | 8/1995 | Biedermann et al. |
| 5,498,264 A | 3/1996 | Schlapfer et al. |
| 5,501,684 A | 3/1996 | Schlapfer et al. |
| 5,520,689 A | 5/1996 | Schlapfer et al. |
| 5,534,001 A | 7/1996 | Schlapfer et al. |
| 5,545,165 A | 8/1996 | Biedermann et al. |
| 5,615,965 A | 4/1997 | Saurat et al. |
| 5,672,176 A | 9/1997 | Biedermann et al. |
| 5,716,356 A | 2/1998 | Biedermann et al. |
| 5,725,527 A | 3/1998 | Biedermann et al. |
| 5,741,255 A | 4/1998 | Krag et al. |
| 5,814,046 A | 9/1998 | Hopf |
| 5,873,878 A | 2/1999 | Harms et al. |
| 5,961,517 A | 10/1999 | Biedermann et al. |
| 6,077,262 A | 6/2000 | Schlapfer et al. |
| 6,106,526 A | 8/2000 | Harms et al. |
| 6,110,172 A | 8/2000 | Jackson |
| 6,302,888 B1 | 10/2001 | Mellinger |
| 6,565,565 B1 | 5/2003 | Yuan et al. |
| 6,755,829 B1 * | 6/2004 | Bono et al. .................... 606/61 |
| 2001/0025180 A1 | 9/2001 | Jackson |
| 2002/0120272 A1 | 8/2002 | Yuan et al. |
| 2002/0143332 A1 | 10/2002 | Lin et al. |
| 2004/0030337 A1 | 2/2004 | Alleyne et al. |

FOREIGN PATENT DOCUMENTS

| | | |
|---|---|---|
| JP | 2001-276086 | 10/2001 |
| WO | WO 00/19923 | 4/2000 |

* cited by examiner

LOCKING CAP ASSEMBLY FOR SPINAL FIXATION INSTRUMENTATION

CROSS REFERENCE TO RELATED APPLICATION

This application is a continuation of U.S. patent application Ser. No. 09/667,937 to Bono et al., filed on Sep. 22, 2000 now U.S. Pat. No. 6,755,829, and entitled "Lock Cap Anchor Assembly for Orthopaedic Fixation," which application is incorporated herein by reference in its entirety.

BACKGROUND OF THE INVENTION

The present invention relates to orthopedic fastening systems and to mechanisms for securing and locking a linking or stabilizing element, such as a rod, to a bone screw having a slotted head that receives the rod therein. It also relates to structures or anchor assemblies having such a slotted or open head for receiving a rod, wherein the slotted portion extends from a hook, plate, bracket or positioning arm.

A number of such structures are known. Thus, for example, the widely used Harms T-plate used for stabilizing the cervical vertebrae has a projecting slotted bolt adapted to receive a rod or cable through the slot and clamp down by screwing a nut along the bolt to bear down against the rod. Several patents show holding structures for a fixation rod that are incorporated in the head of a screw, as in U.S. Pat. No. 5,672,176, or into a small offset plate which itself may be fastened to the bone, as shown in published International Application WO96/28105. Other systems involve hooks, transverse rod connectors, or tandem connectors. Various tools have been provided for these systems to enable the surgeon to bend and shape the rod to a desired contour in situ, to position the rod in the slot of a bolt or head, and to secure the rod in position.

Because the rod is the stabilizing member which provides a precise contour, spacing or connection between one or more vertebrae, bones or bone fragments, alignment is quite critical, and the ability to pass the rod through two or more connecting assemblies requires various actions to form and shape the rod, or align the receiving structures at defined positions or path before final clamping is effected. This may involve positioning and removing the rod several times to check and adjust the degree of alignment. Thus, it is generally desirable to have a closure or secure locking mechanism that may be effected with simple installation steps.

One generally accepted locking mechanism simply involves an internally threaded locking nut that may be tightened down along the axis of the screw or slotted shaft, using a tool such as a socket wrench. Another commercial device employs a bayonet-mount cap that captures or is captured by the screw head, as in U.S. Pat. Nos. 5,346,493 and 5,257,993. Another system utilizes a cap element with a dovetail or dovetail channel that slides over the rod to close the top of the slot and wedge the rod firmly in position. This latter construction involves no rotation of threaded members, but has the disadvantage that a certain amount of unobstructed lateral space along the rod adjacent to the connection point is necessary for the sliding installation of the closure cap. Furthermore, the cap inserts or sliding wedge closures, while they eliminate the need for awkward screwing or rotational motion during installation, cannot be used with some existing reduction screws, translation hooks or other common hardware having lengthy protruding guide members, reduction tabs or the like. Moreover, the wedge/cap closures are a specialized component that may require the user to switch entirely over to a proprietary line of orthopaedic hardware if he is to utilize the full range of hook, tab, plate and screw fixation points that may be required in spinal surgery. While the closure systems described above have in at least some instances been quite successful, it would be beneficial to provide a closure assembly that could securely lock down a rod down while requiring only a small number of locking steps by the surgeon and small lateral clearances surrounding the closure.

SUMMARY OF THE INVENTION

One or more of these and other desirable traits are achieved in accordance with the present invention by a fixation assembly wherein a closure cap fits over an opening to close a rod-receiving slot of a fixation screw, hook, post or other anchor assembly, and capture the rod therein. A set screw can be threaded through the cap and tightened against the rod to further clamp it in the assembly. In one embodiment, the closure cap extends over and around the head of the rod-receiving assembly, which may, for example include a slotted shaft, post or head, and the cap is adapted to lock together therewith by limited rotation. This may be accomplished in one embodiment construction by arranging the cap to have a set of sector rim protrusions positioned to fit through a corresponding set of protruding bosses or partial flange segments located on the head, and to rotate into opposition therewith for securing the cap onto the top of the fixation screw. The protrusions or flange segments are angled, along the radial direction, so that they bear against each other and jam when rotated, thus cannot slip out of engagement. The opposed segments tighten and lock the cap against the head when the cap is rotated through a partial turn of about twenty-three degrees of arc, like a flange-locking bayonet mount. The cap may have a rim that extends over the outside of the bolt head to engage external flange segments on the head. In a preferred embodiment, the mating portions may located internally in the head, with flange segments projecting radially inward from the perimeter, and the cap fitting between segments in the head of the bolt and locking with a twist-in motion to capture a rod in the opening. A hold-down set screw threads through a central opening in the cap and tightens down against the rod to clamp the rod firmly in place. The closing and clamping may each be effected by a driver tool that operates along the axis of the assembly and requires little or no side clearance to rotate either the cap or the set screw. In the case of the external, twist□ on cap, the limited degree of rotation allows the cap to also include slots through the cap to accommodate reduction tabs extending upwardly from the underlying screw or anchor member. The quick-twist closure cap assemblies of the invention may be adapted to a wide range of screw, hook, eye, plate, connector and other anchor assemblies for rod, cable and other linking elements.

BRIEF DESCRIPTION OF THE DRAWINGS

The invention will be more fully understood from the following detailed description taken in conjunction with the accompanying drawings.

DETAILED DESCRIPTION OF THE INVENTION

The invention and its range of embodiments will be better understood following a brief description of prior art, illustrating approaches to one- and two-part anchor assemblies, as well as certain common constructions.

Figure 1A:
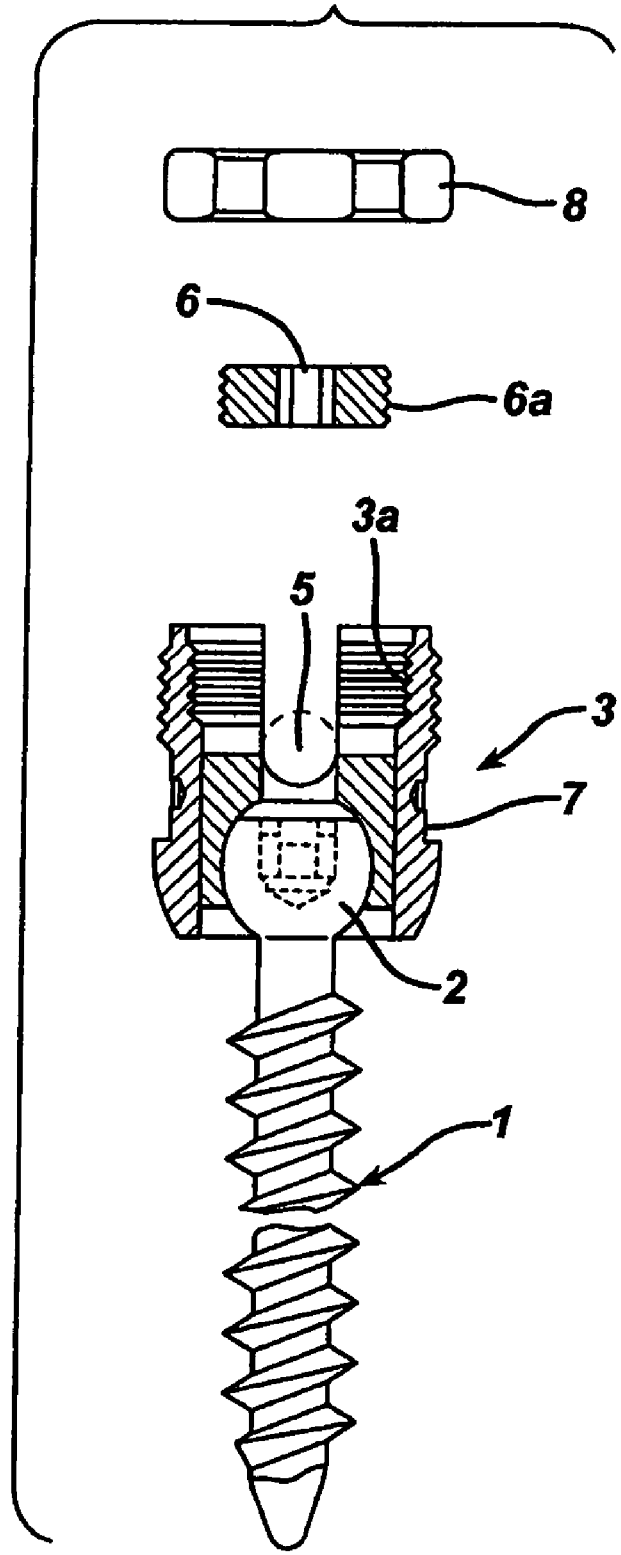
FIGS. 1A–1C schematically illustrate various spinal fixation rod anchor assemblies of the prior art.
Figure 1B:
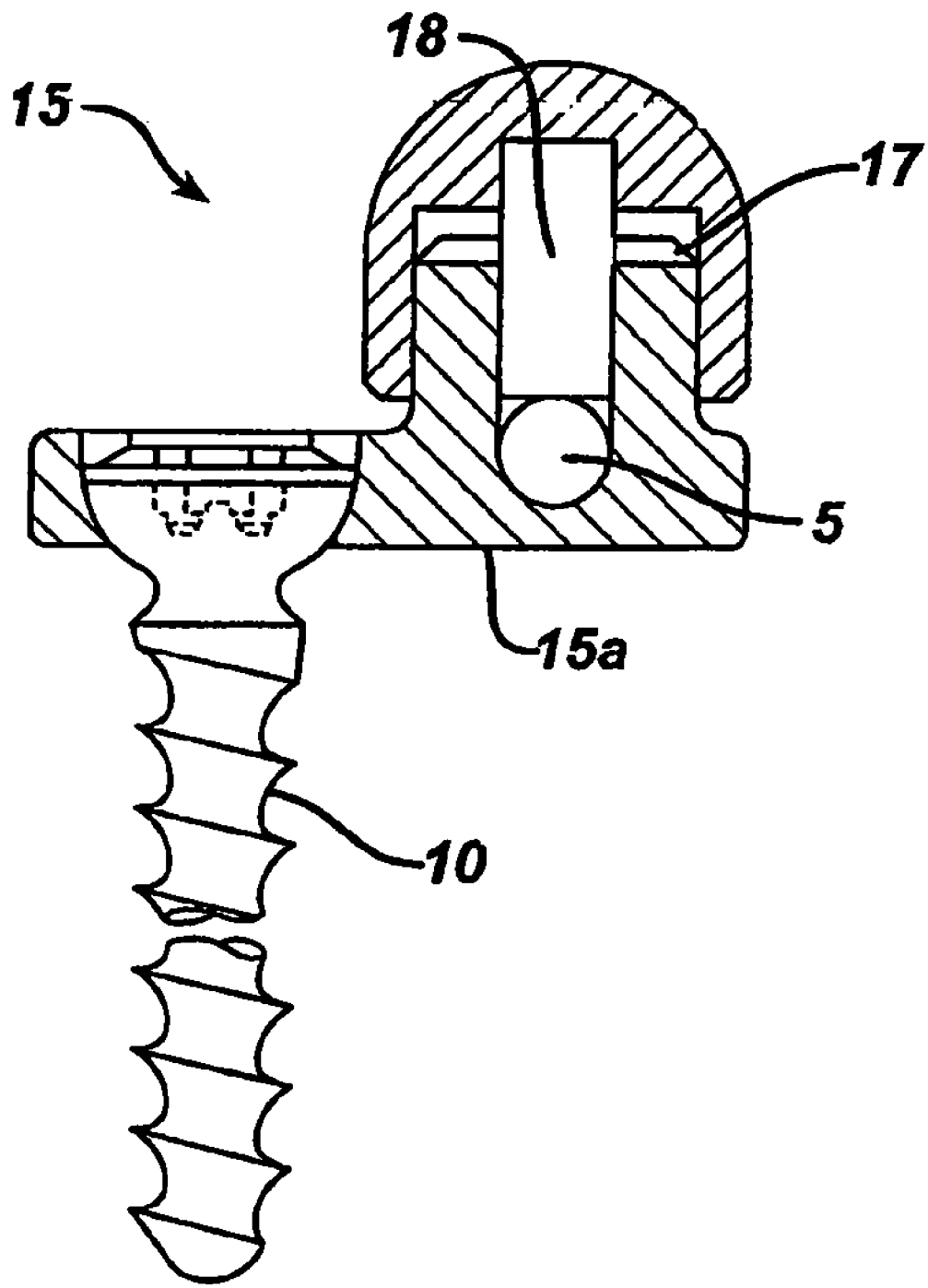
Figure 1C:
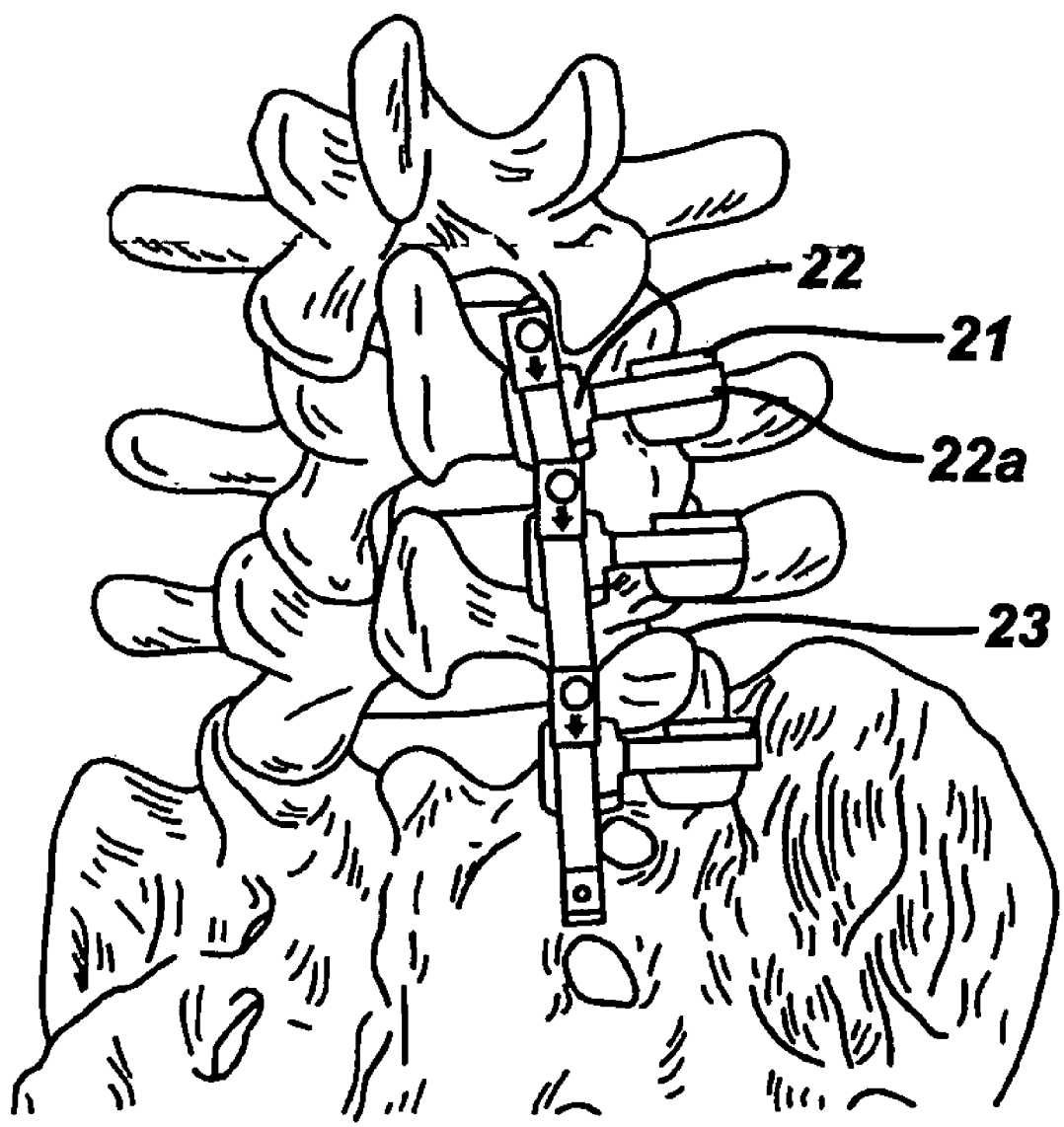

FIGS. 1A–1C illustrate prior art anchor mechanisms for securing a fixation rod as used in spinal fixation. FIG. 1A illustrates an anchor screw, while FIG. 1B shows an offset tab having a slotted post for receiving the rod and FIG. 1C shows a combined system in which anchor screws secure rod-shaped offset elements that, in turn, each terminate in an end that grips a common fixation rod. In the anchor screw of FIG. 1A, a screw 1 with a rounded head 2 carries a slotted top member 3 into which a rod 5 shown in phantom is clamped by screwing down a threaded press ring or set screw 6. The press ring 6 is turned by engagement along its central portion e.g., by an Allen wrench, and has external threads 6a which fit corresponding internal threads 3a of the top member 3. A separate body 7 fills the space between the inner wall of the top 3 and the ball head 2 of the screw 1, so that when the rod is pressed down by the member 6, the screw head is firmly gripped and all parts are rigidly held together. An external nut 8 threads over the outside of the top to further strengthen and lock the assembly. For this prior art anchor member, the screw 1, the press member 6 and the nut 8 may all be installed with a straight tool, such as an Allen wrench or socket wrench, inserted directly along the axis of the screw.

FIG. 1B shows another anchor assembly 15 for receiving a fixation rod 5. In this assembly, an offset tab construction having a body 15a that is anchored by a conventional bone screw 10 and including a slotted post (not numbered) for receiving the rod, is closed by a cap nut 17 which carries a pressure member 18 centrally thereon to press down against the rod 5 as the nut is tightened. In each of these two constructions, the member 6 or 17 for clamping down against the rod 5 installs by rotational movement.

Another prior art anchor assembly is illustrated in FIG. 1C. In this article, a slotted body 21 or 22 is carried either on a bone screw (not visible in the Figure) or on a short length of offset rod 22a. In both cases, the slotted body 21 or 22 receives a rod and clamps it tightly. In this assembly the slotted head member 21 or 22 has angled or dovetailed walls at its upper portion, and a correspondingly shaped sliding cap member 23 is pressed along the dovetail into the upper region, sliding along the axis of the slot to close the slot and wedge firmly against the rod passing therethrough. As noted above, this construction has a disadvantage that a lateral clearance along the length of the rod is necessary for movement of the closure member 23 into position. Other constructions are shown in U.S. Pat. Nos. 5,346,493, 5,257, 993 and elsewhere.

Thus, the art includes both one-piece, and many-piece anchor assemblies, and these may look like screws, or may be specialized elements that are themselves to be anchored by another assembly. As described further below, the present invention provides a closing and fixing mechanism of enhanced utility, with a structure adaptable to much of this broad range of hooks, screws, connector assemblies and other orthopaedic anchor hardware involving one or more rod, cable, wire or other linking elements.

Figure 2:
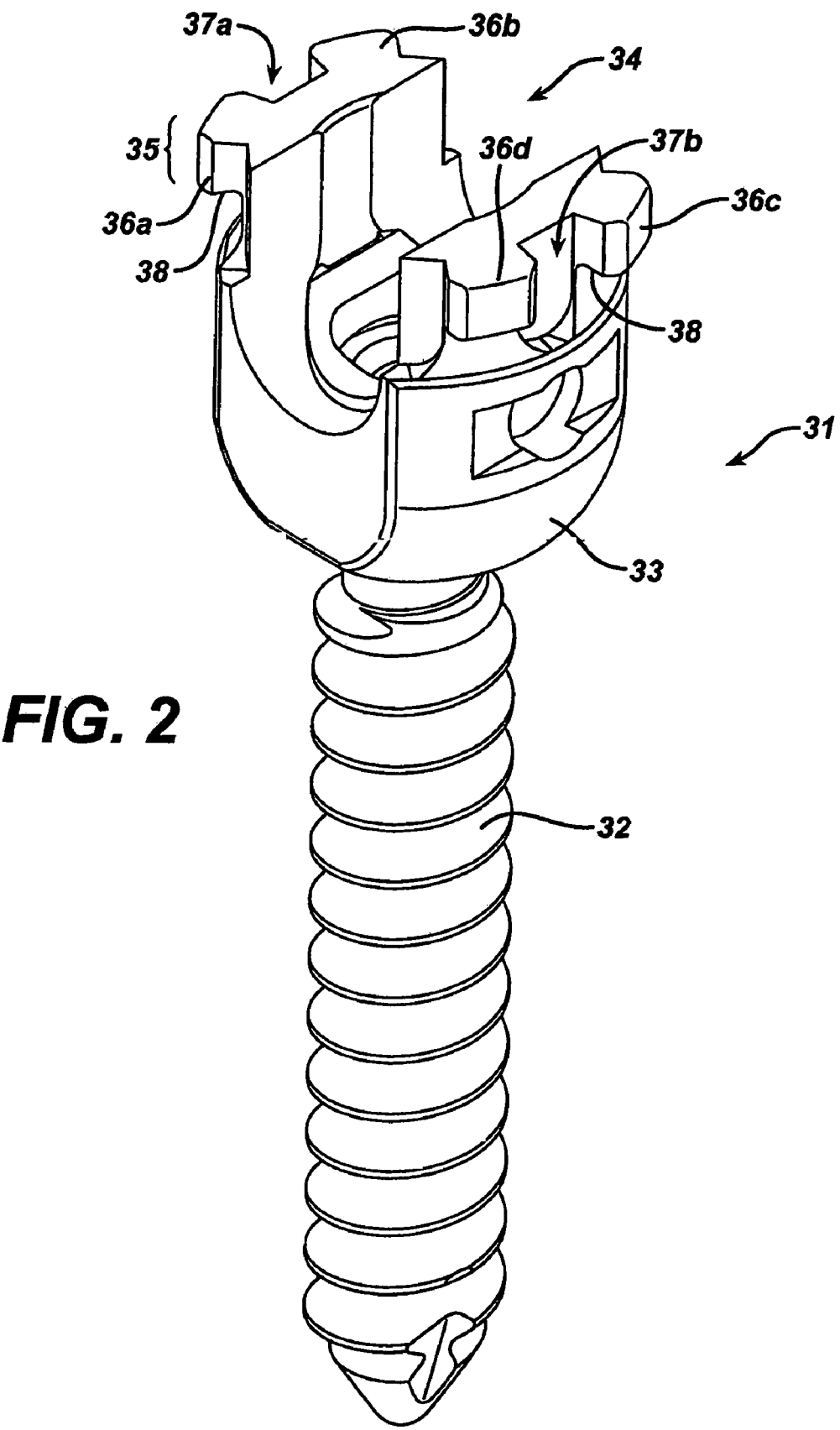
FIG. 2 shows an embodiment of an anchor screw of the present invention.
Figure 3:
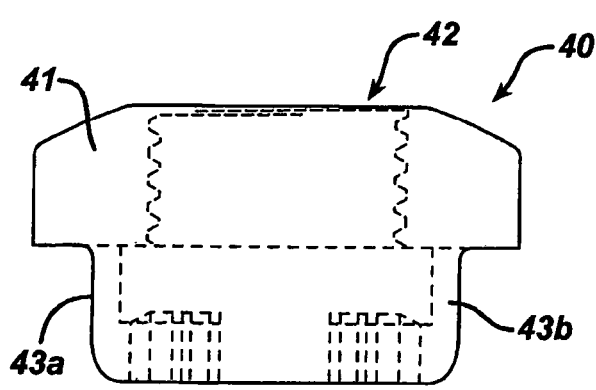
FIGS. 3 and 3A–3C show views of a closure cap utilized with the anchor screw of FIG. 2 in accordance with the present invention.
Figure 3A:
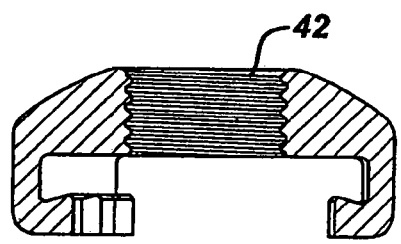
Figure 3B:
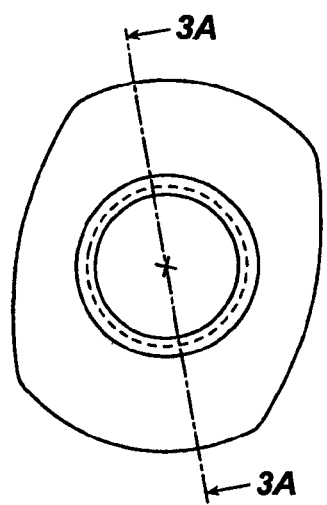
Figure 3C:
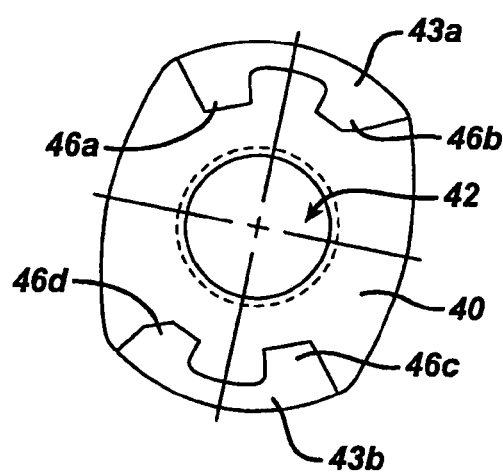

FIG. 2 illustrates a first embodiment of an anchor screw assembly 31 of the present invention. As shown, the anchor screw assembly 31 includes a screw 32 and a top member 33 which may be integral with the screw or, like the prior art construction of FIG. 1A, may be a separate head member that secures to the proximal end of the screw 32. The top member 33 includes a slot indicated generally by 34 for receiving a rod, and contains at its uppermost region 35, a plurality of segmented or partial flange members 36a, 36b, 36c, 36d which extend radially outward from its perimeter and have respective slots or spaces 37a, 37b therebetween. As further shown in FIG. 2, each of the flange segments 36a, 36b, 36c, 36d has a lower surface 38, as best seen in the end views of flange segments 36a and 36c, that engages a closure cap 40 (FIGS. 3A–3C). While not shown, one or more of the flange segments or cap may include a notch, detent or catch or a jamming feature, to prevent rotation in the opposite sense.

The anchor screw or hook 31 of FIG. 2 is used in conjunction with a closure cap 40 which is shown in an upward-facing view, from below, in FIG. 3C. The cap 40 fits over and around the upper portion 35 of the slotted, rod receiving top member. As shown FIG. 3, the cap 40 includes a body 41 having a central threaded bore 42 extending therethrough and a pair of dependent side members 43a, 43b on opposed peripheral sides thereof which extend downward on opposed sides surrounding the outer circumference of the top member 33. Each of the side members 43a, 43b carries mating inwardly directed protrusions 46a, 46b, and 46c, 46d, respectively, which are spaced apart and positioned to correspond to the segmented flange members 36a–36d of the screw head. In particular, the protrusions 46a to 46d are positioned below the main body of the cap 41 by an amount corresponding to the maximum thickness of the flange segments 36a to 36d, and are rotationally offset so as to pass down through the gaps between segments and rotate into gripping engagement around the segments by a partial rotation of the cap 40 about the screw head assembly or top member 33, in the manner of a bayonet mounted lid closure. This secures the cap 40 on the top member closing the slot to prevent movement of the rod or cable from the head along the axial direction of the screw 32. A set screw (not shown) threaded through the aperture 42 is then tightened to clamp firmly down against the rod, cable or other linkage captured in the slot 34 (FIG. 2).

Advantageously, with the foregoing construction, the anchor screw 31 and the closure assembly 40 as well as the set screw (not illustrated) all install by simple rotational movement of a tool that extends directly along the axis of the screw. Moreover, as illustrated, the initial locking of the cap on the head assembly is effected by a small rotational movement, substantially less than one-half turn, which corresponds approximately to the length of the lower surface 38 of one flange segment, or about 20 degrees of rotational movement. Thus a very slight movement is sufficient to capture the rod 5 (FIGS. 1A–1C) within the slot 34 during initial setup or fitting of the fixation rod.

This twist-lock flanged anchoring assembly with a cap structure of the present invention is readily adapted to diverse other fixation screws of known design, and thus in various alternative embodiments and adaptations may carry forward the advantages of those other designs. Thus, for example, the locking cap assembly of FIGS. 2–3 of the invention may be adapted to an anchor assembly such as a reduction screw, anchor screw, or hook in which the anchor member possesses protruding reduction tabs that extend upwardly from the head of the anchoring assembly.

Figure 4:
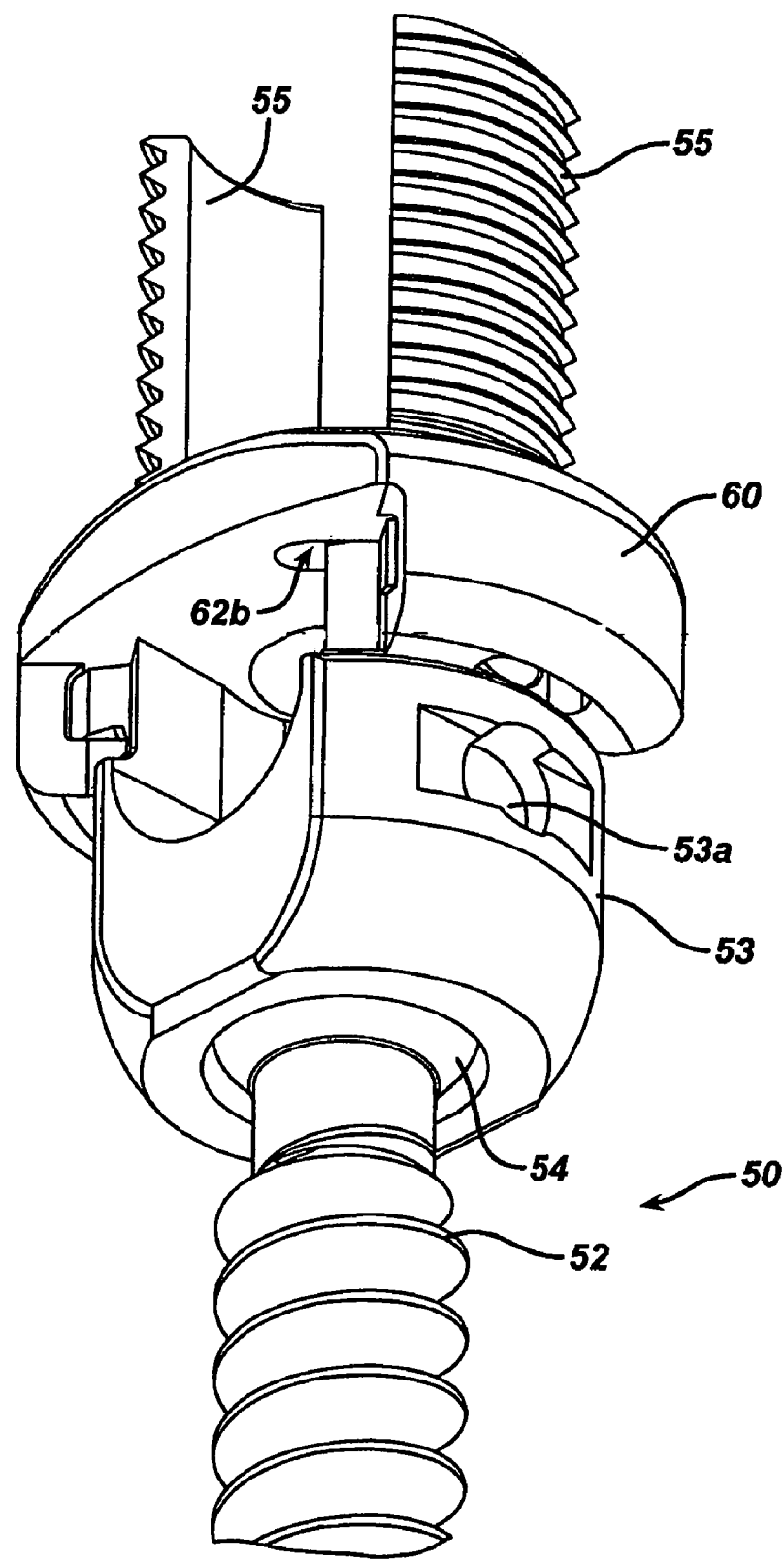
FIG. 4 shows a second embodiment of an anchor member and closure cap of the invention.

Such an embodiment 50 is shown in FIG. 4. In this embodiment, the head 53 of the anchor assembly has a pair of reduction tabs 55 extending upwardly from the sides of the slot. In this case, the invention contemplates a closure cap 60 with a rim-engaging securing structure similar to that of cap 40 for engagement by a small rotational motion, but the cap structure further includes a pair of arcuate slots 62a, 62b located in its central region and sized for passage of the reduction tabs 55 or other protruding head structure therethrough. Each of the slots 62a, 62b extends past the edges of the tabs 55, permitting sufficient rotation of the cap to lock the cap in position. The structure of the cap itself strengthens or supports both the surrounding wall of the rod receiving slot, and the thin-walled tabs 55 which rise therefrom, while leaving the central on-axis region above the cap entirely unobstructed for insertion, for example, of a set screw along an axial direction, and permitting line-of-sight access by a driver for installation.

In any of the foregoing constructions, the rod-receiving head assembly or top member 33, 53 may be integral with the anchor screw 35, 52 or may be constituted by a separate slotted head member that fits about the top of the screw to grip the rod or other connecting linkage. Thus, the invention applies to diverse anchors, hooks, monoaxial screws, transverse connections or tandem connections, slotted connectors or the like.

FIG. 4 illustrates this aspect of the invention for a reduction tab embodiment of which the head is separate from the screw. As shown, the anchor screw assembly 50 has a screw body 52 with an enlarged head 54 which may, for example, have an Allen or other female socket formed therein (not shown) for applying torque along the axis of the screw to insert the screw in bone. A slotted top member 53 having a tapered interior bore is first fitted over the head 54, receiving the screw body from above, capturing the enlarged ball head 54 of the screw therein. A compressed member (not shown) which may be similar to element 7 of FIG. 1A, may be provided to create a binding fit, and this element may be fixed in place, for example, by swaging at opposed surface relief drillings 53a, or it may fit by simple compression. The provision of top member 53 as a separate head structure that is loosely fixed to, but originally decoupled from, the screw 52 in this manner allows the slot angle to be set at a later stage of installation, while avoiding the risk of losing separate small components.

Figure 4A:
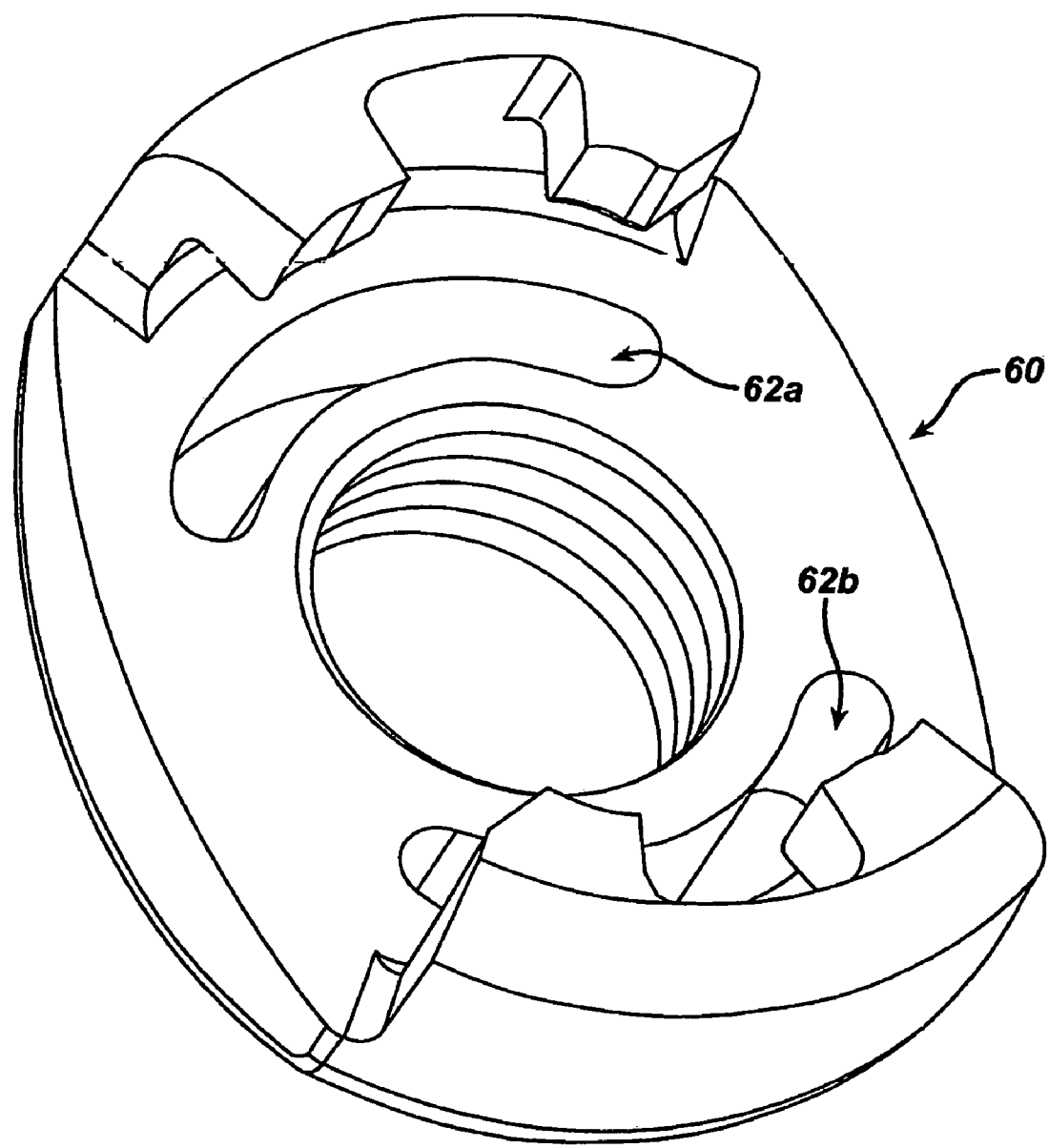
FIG. 4A is a perspective view from below of the cap of FIG. 4.

The cap 60 of this embodiment, which is shown in a perspective view from below in FIG. 4A, is similar to that of the first described embodiment, but includes arcuate slots 62a, 62b to accommodate the projecting reduction tabs. In each case, the cap member having a dependent locking rim that grips the outside of the slotted top and closes the slot by a partial rotation, provides a simple and unobstructed procedure for closing the head of the anchor and capturing the rod, cable or other linkage in the anchor assembly and clamping the linkage while fixing the orientation.

Figure 4B:
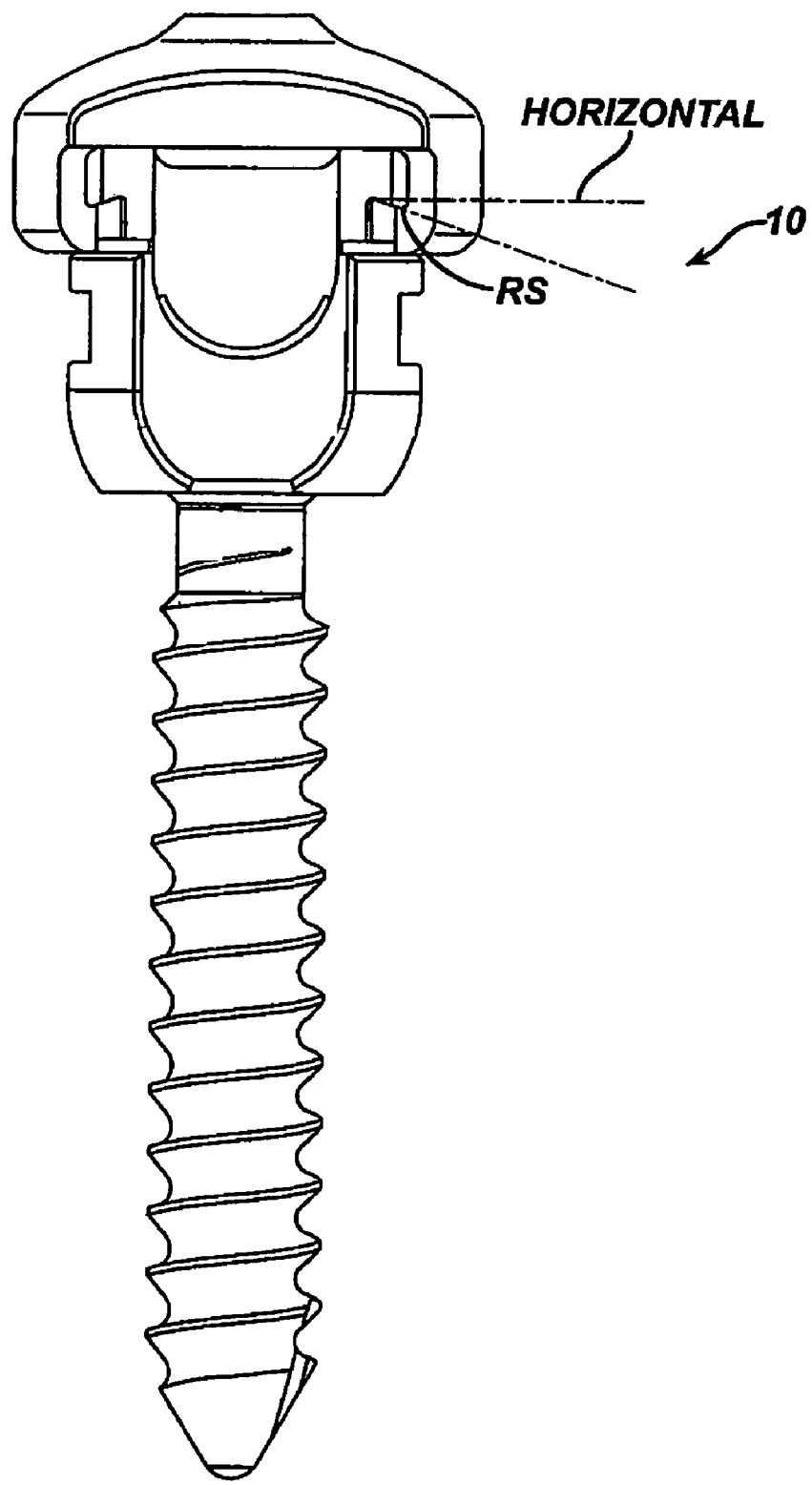
FIG. 4B illustrates details of the anchor member of FIG. 4.

In each of the foregoing illustrated embodiments, the cap extends radially beyond the outer radius of the anchor screw head assembly, and has a rim that extends to a greater diameter, and slides between the segmented flange bosses 36 to rotate into a captured position which closes the slot and captures the rod or other linkage within the head of the anchor assembly. A radial slant "RS" at an angle Θ may be provided on one or more faces of the opposed locking members as shown in the detail FIG. 4B to assure that they cannot slip radially outward under pressure.

In further embodiments, the invention contemplates a twist-on cap member which fits within the head of the anchor assembly rather than extending over and locking on the outside of the head.

Figure 5:
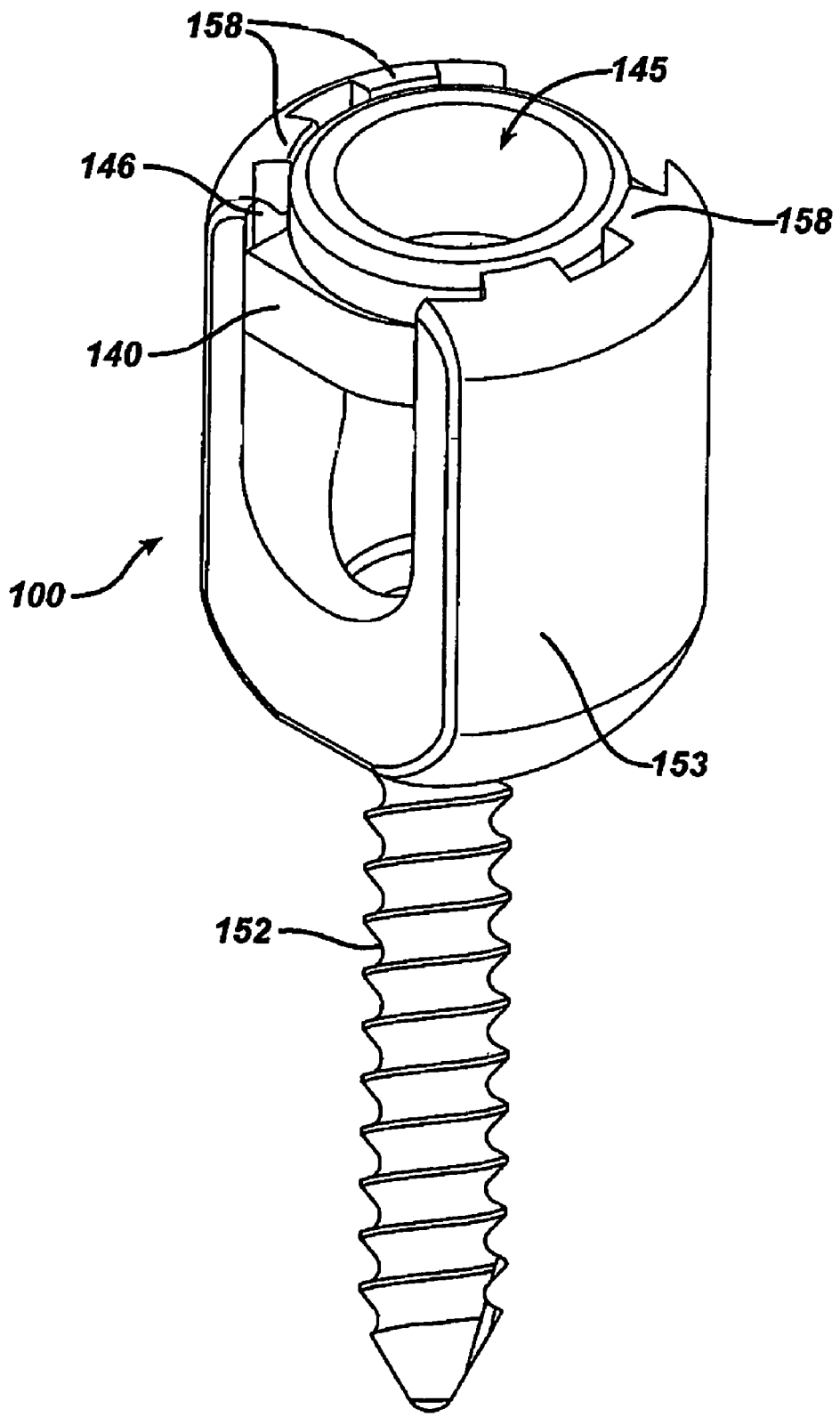
FIG. 5 shows a third embodiment of an anchor member and closure cap of the invention.

FIG. 5 illustrates one embodiment 100 of such a twist-in anchor closing mechanism. As shown, the anchor assembly 100 has a screw portion 152 for anchoring in bone, and a head portion 153 for receiving the rod, cable or other linkage. A closure cap 140 closes the slotted end of head 153. As in the previously described embodiments, the screw and head may be separate assemblies, in which case the upper portion of the screw preferably has a ball end as described above that allows the head to pivot about the axis of the screw and achieve a further degree of freedom in angular orientation before clamping down. As with the earlier described embodiments, the cap or closure portion 140 may have a central bore 145 which is internally threaded to accommodate a set screw to further clamp the rod in the slot; however, to simplify the drawing, threads are omitted from FIG. 5.

The internal closure cap 140 has a plurality of radially protruding flange segments 146, of which one is visible in the Figure, and the cap is pushed downwardly on the head so the respective inward and outward directed segments pass between each other, in a manner similar to the above-described embodiments. Thus, the segments 146 fit between corresponding inwardly protruding segments 158 of the head 153 and lock thereagainst by a small rotation of the cap 140.

Figure 6A:
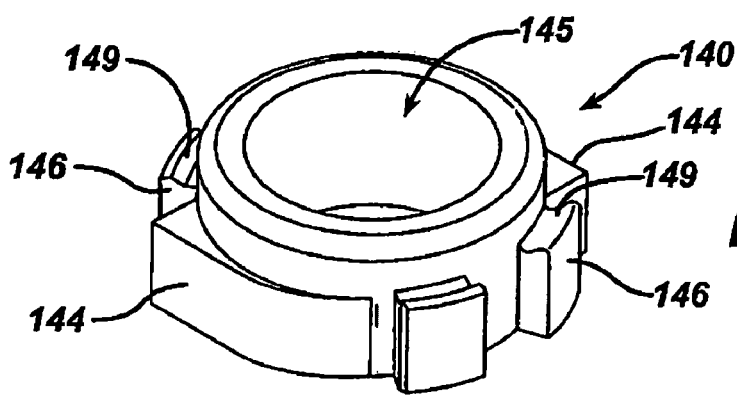
FIGS. 6A, 6B and 6C illustrate the cap and head structure, respectively, of embodiment of FIG. 5 in greater detail.
Figure 6B:
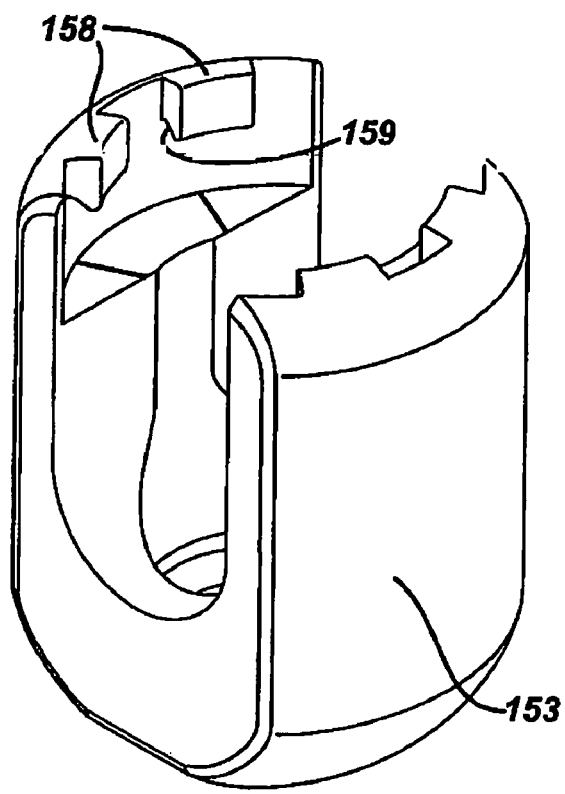

FIGS. 6A and 6B illustrate the structure of the twist-in cap 140 and the slotted head 153 in greater detail.

Figure 6C:
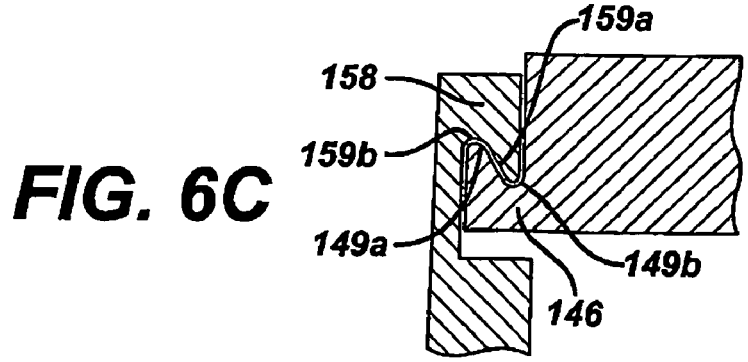

FIG. 6A shows the closure cap 140, and FIG. 6B shows the head assembly 153, of an internal closure locking cap of FIG. 5. As shown, the head assembly 153 of the anchor screw has a plurality of internally projecting bosses 158 and the closure cap 140 has corresponding outwardly projecting bosses 146. Respective bosses 146, 158 are dimensioned such that the cap 140 may be pushed downwardly between spaces of corresponding bosses to position the upper surface 149 of the cap bosses below the lower surface 159 of the retaining head bosses 158. As shown in FIGS. 6A and 6B, these mating contact surfaces are angled or sloped downwardly with a radial slant "RS" at an angle Θ (illustrated in FIGS. 5 and 6B) toward the center. In this way, when the cap 140 is rotated to place opposed bosses in an engagement with each other, the cap exerts a net inwardly directed force on the head to prevent spreading of the retaining slot. The contours of the sloped ends are relatively sharply defined, effectively forming a circumferential ridge 149a, 159a and groove 149b, 159b on each of the respective components (FIG. 6C). The ridge of one part fits in the groove of the other, so that the closure is centered and grips over a substantial contact area.

As best seen in FIGS. 5 and 6A, the twist-in cap has opposed edge flats 144 which may provide a contact or engagement surface for a tool such as a wrench used for turning the cap upon installation. Each of the flats 144 has a corner to prevent over-rotation of the cap, so that upon insertion it rotates to exactly position the respective bosses 146, 158 opposite each other as the anchor assembly is closed. The set screw is then tightened to secure the fixation linkage captured in the slot.

Figure 7A:
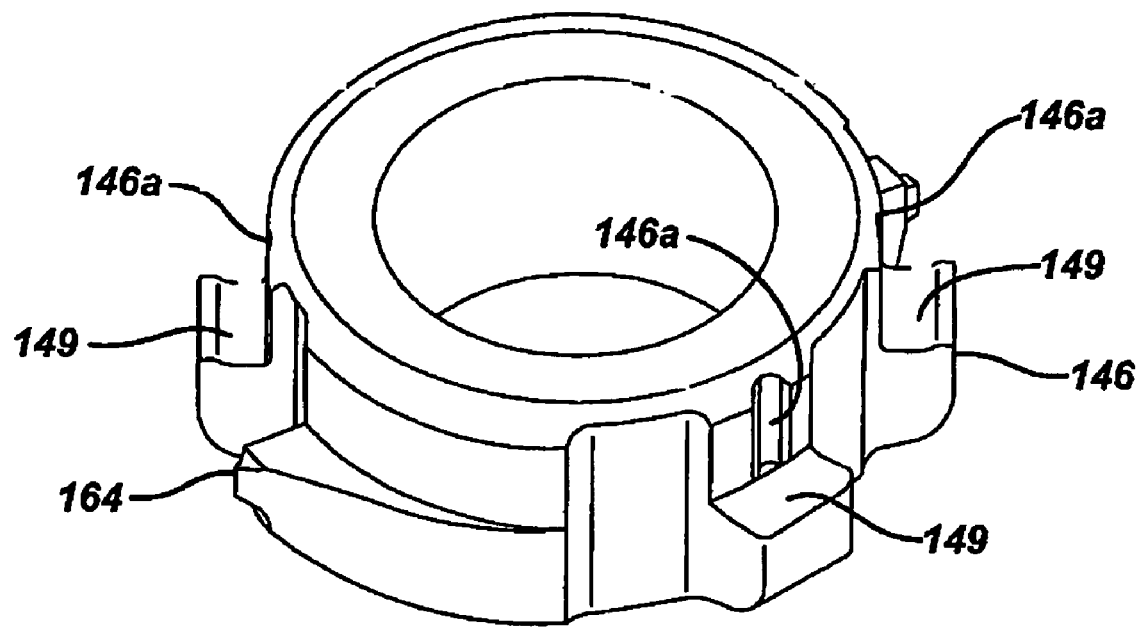
FIGS. 7A, 7B and 7C illustrate cap, head and assembled structure, respectively, of another internal twist cap embodiment.
Figure 7B:
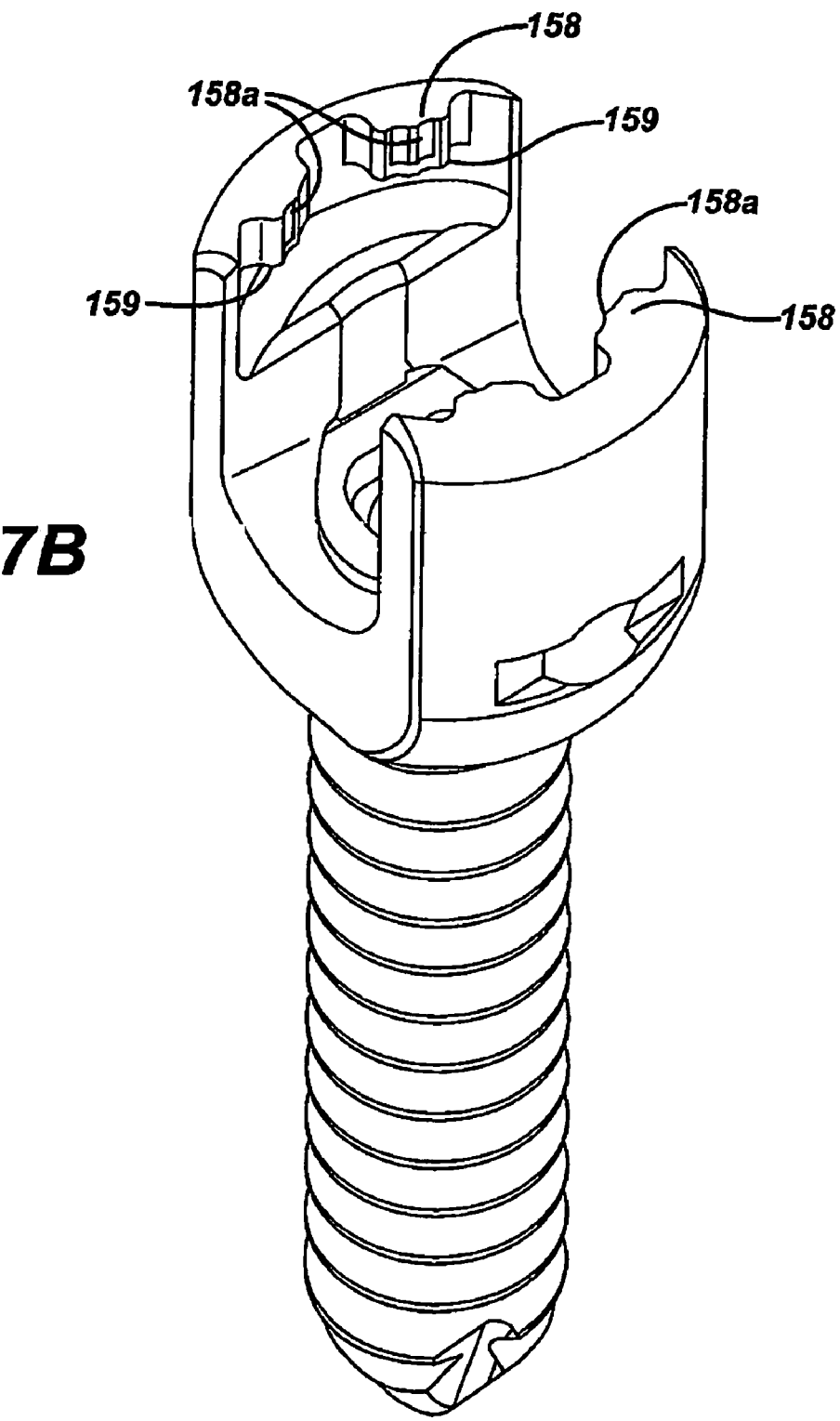
Figure 7C:
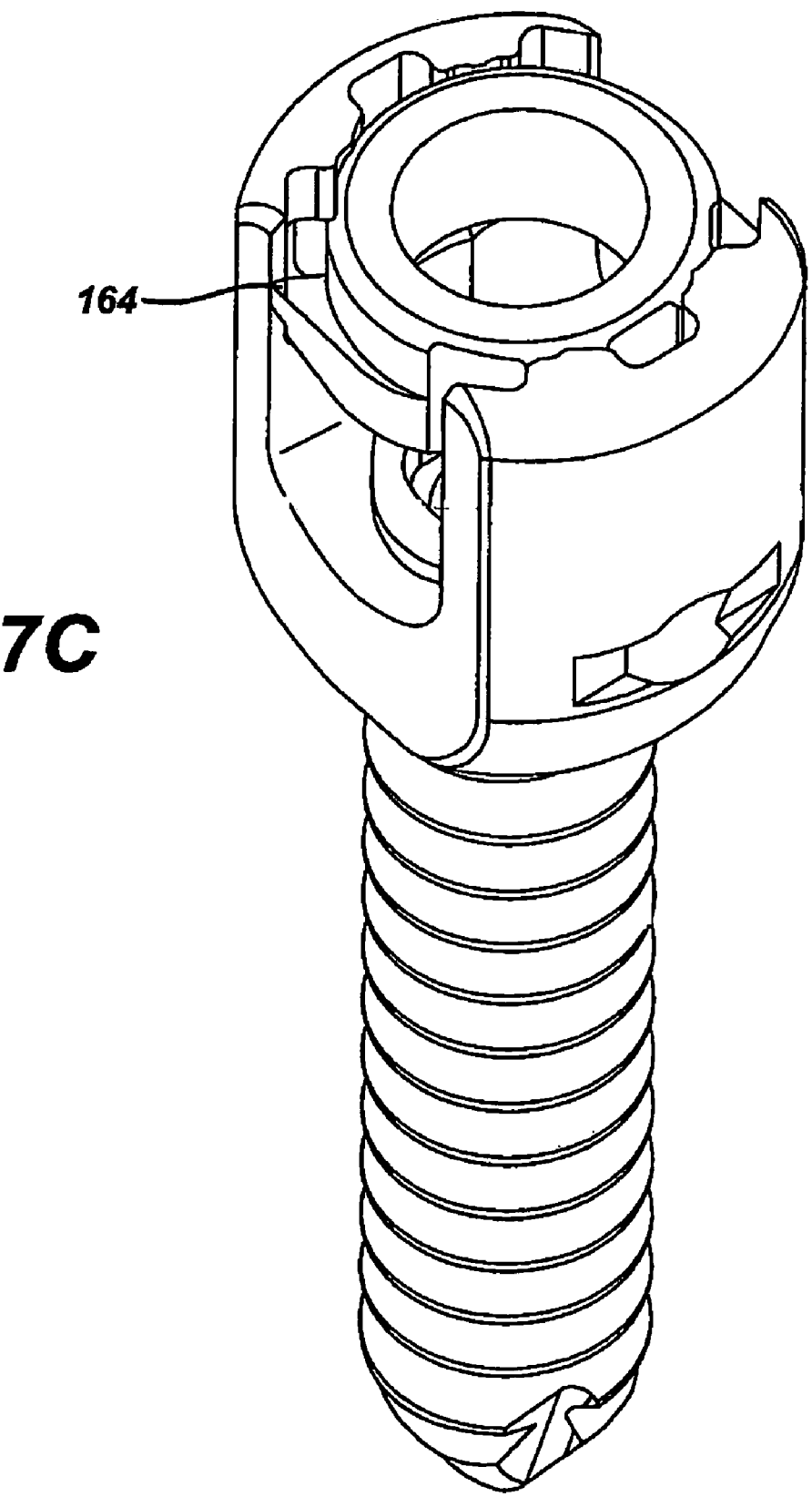

FIGS. 7A–7C illustrate another embodiment of a twist-in closure cap and spinal anchor assembly, having an anchor screw, a slotted head and a twist-in closure cap. As in the previously described embodiments, the screw and head may be separate assemblies, e.g., to achieve freedom in angular orientation before clamping down. The head and cap structure similarly may be adapted to spinal anchor assemblies of other types, such as transverse connectors, anchor plates and other link-receiving hardware. As with the earlier described embodiments, the cap may have a central bore which is internally threaded to accommodate a clamping set screw to lock and immobilize the linkage once it has been captured in the slot; however, to simplify the drawing, threads are omitted from FIGS. 7A and 7C.

In this embodiment, the radially protruding bosses or flange segments 146 of the cap, and the inwardly protruding bosses 158 of the head are arranged so the respective inward and outward directed segments pass between each other, when the cap is pushed downwardly into the head, in a manner similar to the above-described embodiments. Thus, the segments 146 fit between corresponding, inwardly protruding segments 158 of the head and lock thereagainst by a small rotation of the cap. In addition, the twist-lock mechanism may be configured to exert enhanced contact force in a detent region when the clamp screw is tightened down.

As shown in FIGS. 7A–C, this is achieved in a presently preferred embodiment by providing lower and upper contact faces 159, 149 on the segments 158, 146 of the head and cap, respectively, that slope downward toward the center so that when the set screw is tightened the upward force on the cap draws the segments 158 inward and upward. A vertically-oriented protruding ridge 158a and mating groove 146a are formed on the head and cap, on or directly above the corresponding flange region of each, so that the ridge 158a on the head is urged inwardly against the groove surface of the cap. This effectively locks the rotational detent to prevent any rotational movement of the cap once the set screw is tightened.

As further seen in FIGS. 7A and 7C, the twist-in cap has a protruding stop face 164 that contacts the head and prevents over-rotation of the cap when it is turned to close the head. Thus, upon insertion the cap rotates (clockwise as shown) to position the bosses 146, 158 exactly opposite each other as the anchor assembly is closed. The set screw is then tightened to secure the fixation linkage captured in the slot.

The invention being thus disclosed and illustrative embodiments depicted herein, further variations and modifications of the invention will occur to those skilled in the art. All such variations and modifications are considered to be within the scope of the invention, as defined by the claims appended hereto and equivalents thereof.

What is claimed is:

1. A spinal anchor assembly for securing a spinal fixation element, comprising:

an anchor element adapted for attachment to bone and defining a central longitudinal axis, the anchor element having an open slot for receiving the spinal fixation element, side walls on opposed sides of the open slot, and a plurality of anchor flange segments extending from the side walls in a direction generally transverse to the central longitudinal axis, the anchor flange segments each including an inferior contact surface extending in a direction with respect to the central longitudinal axis that defines a radial slant; and a closure element for closing the open slot in the anchor element and applying pressure to the spinal fixation element to capture the spinal fixation element within the open slot, the closure element including a closure body and a plurality of closure flange segments extending from the closure body in a direction that is transverse to the anchor element central longitudinal axis when the closure element is placed in the open slot, each closure flange segment including a superior contact surface extending at an angle corresponding to the radial slant when the closure element is placed in the open slot so that the closure flange segment superior surfaces engage the anchor element flange segment inferior surfaces when the closure element is placed in a closed position in the anchor element open slot;

wherein the anchor element and closure element flanges are configured to permit the closure element to be placed into the open slot in the anchor element in an open position and to be twisted into the closed position, and the radial slant is configured so that, when the closure element is in its closed position and pressure is applied to secure the spinal fixation element within the open slot in the anchor element, the anchor element and closure element flanges are drawn together.

2. The assembly of claim 1, wherein the anchor element comprises a pedicle screw.

3. The assembly of claim 1, wherein the anchor element comprises a polyaxial pedicle screw.

4. The assembly of claim 1, wherein the anchor element comprises a hook.

5. The assembly of claim 1, wherein at least one anchor flange segment is provided on each side wall.

6. The assembly of claim 1, wherein a plurality of anchor flange segments are provided on each side wall.

7. The assembly of claim 6, wherein the plurality of anchor flange segments provided on each side wall are configured so that the closure element can be moved from the open to the closed position by twisting the closure element by less than or equal to about twenty degrees.

8. The assembly of claim 1, wherein the closure element includes a central clamping element for applying pressure to a spinal fixation element.

9. The assembly of claim 8, wherein the central clamping element is separately tightenable with respect to the closure element.

10. The assembly of claim 9, wherein the assembly is configured so that the closure element can be placed in the closed position to movably capture a spinal fixation element within the open slot and the central clamping element can be separately tightened to fix the position of the spinal fixation element within the open slot.

11. The assembly of claim 8, wherein the central clamping element is rotatably connected to the closure element.

12. The assembly of claim 11, wherein the central clamping member is a central clamping bolt.

13. The assembly of claim 1, wherein a locking element is provided on the closure element.

14. The assembly of claim 13, wherein the locking element is configured to lock upon rotation of the closure element from the open position to the closed position.

15. The assembly of claim 14, wherein, upon locking, the locking element deters the closure element from rotating back to the open position.

16. An anchor assembly for securing a fixation member to bone comprising:
   an anchor element having a bone fixation member, a head with an opening for receipt of a fixation member, and a cap;
   the head and the cap each containing a plurality of radially-protruding elements configured to allow the cap to be placed in the opening when the cap is oriented in a first, open position and to engage each other to hold the cap within the opening when the cap is rotated to a second closed position;
   wherein the engagements between the head radially-protruding elements and the cap radially-protruding elements when the cap is placed in the closed position are angled along a radial direction so that the head radially-protruding elements and the cap radially-protruding elements bear against one another when a pressure is applied to the cap by the fixation member so as to draw the head radially-protruding elements and the cap radially-protruding elements together.

17. The assembly of claim 16, wherein the head comprises a plurality of side walls defining an open slot.

18. The assembly of claim 17, wherein the head radially-protruding elements are integral with the side walls of the head.

19. The assembly of claim 18, wherein the head further comprises angled inferior contact surfaces defined by the sidewalls and integral radially-protruding elements.

20. The assembly of claim 19, wherein the inferior contact surfaces are configured to hold the cap within the open slot when the cap is placed in the closed position.

21. The assembly of claim 17, wherein at least radially-protruding element is provided on each side wall.

22. The assembly of claim 17, wherein a plurality of radially-protruding elements are provided on each side wall.

23. The assembly of claim 22, wherein the plurality of radially-protruding elements provided on each side wall are configured so that the cap can be moved from the open to the closed position by twisting the closure element by less than or equal to about twenty degrees.

24. The assembly of claim 16, wherein the cap includes a central clamping element for applying pressure to a spinal fixation element.

25. The assembly of claim 24, wherein the central clamping element is separately tightenable with respect to the cap.

26. The assembly of claim 25, wherein the assembly is configured so that the cap can be placed in the closed position to movably capture a spinal fixation element within the head and the central clamping element can be separately tightened to fix the position of the spinal fixation element within the head.

27. The assembly of claim 24, wherein the central clamping element is rotatably connected to the cap.

28. The assembly of claim 27, wherein the central clamping member is a central clamping bolt.

29. The assembly of claim 16, wherein a locking element is provided on the cap.

30. The assembly of claim 29, wherein the locking element is configured to lock upon rotation of the cap from the open position to the closed position.

31. The assembly of claim 30, wherein, upon locking, the locking element deters the cap from rotating back to the open position.

32. The assembly of claim 16, wherein the bone fixation member comprises a pedicle screw.

33. The assembly of claim 16, wherein the bone fixation member comprises a polyaxial pedicle screw.

34. The assembly of claim 16, wherein the bone fixation member comprises a hook.

35. A spinal anchor assembly for securing a spinal fixation element, comprising:
   an anchor element adapted for attachment to bone and defining a central longitudinal axis, the anchor element having an opening for receiving the spinal fixation element, side walls on opposed sides of the opening, and a plurality of inferior surfaces defined on the side walls; and
   a closure element for closing the opening in the anchor element and applying pressure to the spinal fixation element to capture the spinal fixation element within the opening, the closure element including a closure body and a plurality of closure flange segments extending from the closure body in a direction that is generally transverse to the anchor element central longitudinal axis when the closure element is placed in the open slot; and
   a locking element comprising a protrusion and groove provided on the cap and anchor element and configured so that when the closure element is placed into the opening in the anchor element in an open position and is twisted into a closed position in which the closure element flange segments engage the anchor element inferior surfaces to hold the closure in the opening, the protrusion and groove engage so that the locking element deters the closure element from twisting back to the open position.

36. The assembly of claim 35, wherein the closure element includes a central clamping element for applying pressure to a spinal fixation element.

37. The assembly of claim 36, wherein the central clamping element is separately tightenable with respect to the closure element.

38. The assembly of claim 37, wherein the assembly is configured so that the closure element can be placed in the closed position to movably capture a spinal fixation element within the opening and the central clamping element can be separately tightened to fix the position of the spinal fixation element within the opening.

39. The assembly of claim 36, wherein the central clamping element is rotatably connected to the closure element.

40. The assembly of claim 39, wherein the central clamping member is a central clamping bolt.

41. The assembly of claim 35, wherein the inferior contact surfaces extend in a direction that defines a radial slant and the closure flange segments include a superior contact surface extending at an angle corresponding to the radial slant when the closure element is placed in the opening.

42. The assembly of claim 41, wherein the radial slant is configured so that when the closure flange segment superior surfaces engage the inferior surfaces when the closure element is placed in a closed position in the anchor element opening and pressure is applied to secure the spinal fixation element within the opening in the anchor element, the anchor element side walls and closure element flanges are drawn together.

43. The assembly of claim 35, wherein at least one inferior surface is provided on each side wall.

44. The assembly of claim 35, wherein a plurality of inferior surfaces are provided on each side wall.

45. The assembly of claim 44, wherein the plurality of inferior surfaces provided on each side wall are configured so that the closure element can be moved from the open to the closed position by twisting the closure element by less than or equal to about twenty degrees.

46. An anchor assembly for securing a fixation member to bone comprising:
- an anchor element having a bone fixation member and a head, the head having an opening configured to receive a fixation member;
- a locking cap having a plurality of flanges, the flanges configured so that the locking cap can be placed into the opening in the head when the locking cap is oriented in an open position and the fixation member is received within the opening in the head, and to engage inferior contact surfaces defined on the head to hold the locking cap within the head when the locking cap is rotated to a closed position and to thereby block the fixation member from exiting the head; and
- a clamping element disposed on the locking cap, the clamping element being operable to clamp the fixation member to the head to prevent movement of the fixation member with respect to the head
- wherein the head includes at least two side walls and a plurality of flange segments having inferior contact surfaces are provided on each side wall.

47. The assembly of claim 46, wherein the central clamping element is independently operable with respect to the cap.

48. The assembly of claim 47, wherein the assembly is configured so that the cap can be placed in the closed position to movably capture a fixation element within the head and the central clamping element can be independently operated to fix the position of the fixation element within the head.

49. The assembly of claim 46, wherein the central clamping element is rotatably connected to the cap.

50. The assembly of claim 49, wherein the central clamping member is a central clamping bolt.

51. The assembly of claim 46, wherein a locking element is provided on the cap.

52. The assembly of claim 51, wherein the locking element is configured to lock upon rotation of the cap from the open position to the closed position.

53. The assembly of claim 52, wherein, upon locking, the locking element deters the cap from rotating back to the open position.

54. The assembly of claim 46, wherein the inferior contact surfaces are defined in at least one side wall of the head and extend in a direction that defines a radial slant and the cap flanges include a superior contact surface extending at an angle corresponding to the radial slant when the closure element is placed in the opening.

55. The assembly of claim 54, wherein the radial slant is configured so that when the cap flange superior surfaces engage the inferior surfaces when the closure element is placed in a closed position in the anchor element opening and pressure is applied to secure the fixation element within the opening in the anchor element, the anchor element side walls and cap flanges are drawn together.

56. The assembly of claim 46, wherein the plurality of inferior surfaces provided on each side wall are configured so that the closure element can be moved from the open to the closed position by twisting the closure element by less than or equal to about twenty degrees.

57. An anchor assembly for securing a linkage, wherein the anchor assembly comprises:
- an anchor element configured for attachment to a bone, and having a head having an open slot for receiving the linkage, the head including at least two side walls defined at least a portion of the open slot with inferior contact surfaces defined in the side walls; and
- a cap for closing the open slot;
- wherein the head and the cap are adapted to twist-lock together by a partial rotation to cover the slot so as to capture the linkage, and the cap further includes a central clamping member for tightening down to secure the linkage; and
- wherein a plurality of flange segments having inferior contact surfaces are provided on each side wall.

58. The assembly of claim 57, wherein the central clamping element is independently operable with respect to the cap.

59. The assembly of claim 58, wherein the assembly is configured so that the cap can be placed in a closed position to movably capture a linkage within the head and the central clamping element can be independently operated to fix the position of the linkage within the head.

60. The assembly of claim 59, wherein the central clamping element is rotatably connected to the cap.

61. The assembly of claim 60, wherein the central clamping member is a central clamping bolt.

62. The assembly of claim 57, wherein a locking element is provided on the cap.

63. The assembly of claim 62, wherein the locking element is configured to lock upon rotation of the cap from an open position to a closed position.

64. The assembly of claim 63, wherein, upon locking, the locking element deters the cap from rotating back to the open position.

65. The assembly of claim 57, wherein the cap includes flange segments that interact with the inferior surfaces in a closed position to close the open slot.

66. The assembly of claim 65, wherein the inferior contact surfaces extend in a direction that defines a radial slant and the cap flanges include a superior contact surface extending at an angle corresponding to the radial slant when the closure element is placed in the closed position.

67. The assembly of claim 66, wherein the radial slant is configured so that when the cap flange superior surfaces engage the inferior surfaces when the closure element is placed in the closed position in the anchor element open slot and pressure is applied to secure the linkage within the open slot in the anchor element, the anchor element side walls and cap flanges are drawn together.

68. The assembly of claim 57, wherein the plurality of inferior surfaces provided on each side wall are configured so that the closure element can be moved from the open to the closed position by twisting the closure element by less than or equal to about twenty degrees.

* * * * *